United States Patent [19]

Stahly et al.

[11] Patent Number: 5,442,117
[45] Date of Patent: Aug. 15, 1995

[54] ENANTIOMERIC RESOLUTION

[75] Inventors: G. Patrick Stahly; Thanikavelu Manimaran, both of Baton Rouge, La.

[73] Assignee: Albemarle Corporation, Richmond, Va.

[21] Appl. No.: 165,619

[22] Filed: Dec. 13, 1993

[51] Int. Cl.$^6$ ............................................. C07B 57/00
[52] U.S. Cl. .................................... 564/304; 564/303
[58] Field of Search ................................ 564/303, 304

[56] References Cited

U.S. PATENT DOCUMENTS

| | | | |
|---|---|---|---|
| 4,831,147 | 5/1989 | Russell | 346/302 |
| 4,865,770 | 9/1989 | Piselli | 562/402 |
| 4,931,587 | 6/1990 | Piselli | 562/401 |
| 4,973,745 | 11/1990 | Blaschke et al. | 562/401 |

OTHER PUBLICATIONS

Collet et al., *Chem. Rev.* 80(3), 215–230 (1980).
Jacques et al., *Enantiomers, Racemates and Resolutions,* Chapter 3, J. Wiley & Sons, New York, N.Y., (1981) 167–213.
Collet, A., "The Homochiral Versus Heterochiral Packing Dilemma", 91–110 in *Problems and Wonders of Chiral Molecules,* Simonyi, M. (Ed.), Akademiai Keado, Budapest (1990).

*Primary Examiner*—Peter O'Sullivan
*Attorney, Agent, or Firm*—Philip M. Pippenger

[57] ABSTRACT

A process for obtaining a substantially pure enantiomer of an hydrocarbyl amine is described. The process utilizes first an enantiomerically enriched mixture the of hydrocarbyl amine obtained from kinetic resolution, diastereomeric crystallization or asymmetric synthesis processes. This enriched mixture is reacted with an inorganic acid producing a salt that has the following properties:

1) has at least one eutectic point;

2) a composition that is not at the eutectic point; and 3) a eutectic composition that is closer to the racemic composition than is the eutectic composition of said hydrocarbyl, or be a solid where the salt is a liquid. A substantially pure, enantiomeric salt is separated, leaving a mother liquor comprising the solvent and the hydrocarbyl amine enriched in the other enantiomer.

16 Claims, No Drawings

ENANTIOMERIC RESOLUTION

FIELD OF THE INVENTION

This invention relates to a process for obtaining highly pure enantiomers of hydrocarbyl amines from a mixture of enantiomers.

BACKGROUND OF INVENTION

The resolution of racemates constitutes the main method for industrial preparation of pure enantiomers. Methods for such resolution include: direct preferential crystallization; crystallization of the diastereomeric salts and kinetic resolution. Pure enantiomers may also be produced by asymmetric synthesis (reaction of a chiral auxiliary or catalyst with a prochiral substrate).

Also referred to as resolution by entrainment, preferential crystallization is widely used on an industrial scale; for example, in the manufacture of α-methyl-L-dopa and chloramphenicol. It is technically feasible only with racemates which are so-called conglomerates and consist of mechanical mixtures of crystals of the two enantiomers. Unfortunately, less than 20 percent of all racemates are conglomerates. The rest are true racemic compounds which cannot be separated by preferential crystallization (e.g., by seeding a saturated solution of the racemate with the crystals of one enantiomer). A conglomerate exhibits a minimum melting point for the racemic composition while a racemic compound does not. Further, a conglomerate is generally viewed as an equimolar mixture of two crystalline enantiomers that are, in principle, mechanically separable. Its phase diagram, i.e. a plot of the melting point versus the enantiomeric composition, displays one sharply defined minimum temperature at a mixture of 50% and 50% which is the eutectic point of the enantiomeric mixture. The success of preferential crystallization depends on the fact that the solubility of the pure enantiomer is less than the solubility of the racemic composition, i.e., the mixture having the lowest melting point is the racemic mixture which is most soluble. For a conglomerate, this is the racemic mixture.

If the racemate is a true racemic compound, a homogeneous solid phase of the two enantiomers co-exists in the same unit cell. These materials may be separated via diastereomer crystallization, which generally involves reaction of the racemate with an optically pure acid or base (the resolving agent) to form a mixture of diastereomeric salts which are then separated by crystallization. Ibuprofen, for example, is a true racemic compound.

Diastereomer crystallization is widely used for the industrial synthesis of pure enantiomers. A typical example is the Andeno process for the manufacture of (D)—(—)-phenylglycine, an antibiotic intermediate, using optically pure camphor sulfonic acid as the resolving agent. Also see U.S. Pat. No. 4,752,417 for a diastereomeric procedure for resolving certain phenylacetic acid derivatives and U.S. Pat. No. 4,973,745 for resolving 2-arylpropionic acids.

The theoretical once-through yield of a resolution via diastereomer crystallization is 50 percent. However, in practice, a single recrystallization produces a composition that is simply an enantiomerically enriched racemate.

Another method for the resolution of racemates is kinetic resolution, the success of which depends on the fact that the two enantiomers react at different rates with a chiral addend.

Kinetic resolution can also be effected using chiral metal complexes as chemocatalysts, e.g., the enantioselective rhodium-BINAP-catalyzed isomerization of chiral allylic alcohols to the analogous prostaglandin intermediates reported by Noyori.

The enantioselective conversion of a prochiral substrate to an optically active product, by reaction with a chiral addend, is referred to as an asymmetric synthesis. From an economic viewpoint, the chiral addend functions in catalytic quantities. This may involve a simple chemocatalyst or a biocatalyst. An example of the former is the well-known Monsanto process for the manufacture of L-dopa by catalytic asymmetric hydrogenation. See Knowles, et al., J. Am. Chem. Soc., 97, 2567 (1975). An example of the latter is the Genex process for the synthesis of L-phenylalanine by the addition of ammonia to transcinnamic acid in the presence of L-phenylalanine ammonia lyase (PAL). See Hamilton et al., Trends in Biotechnology, 3, 64–68, (1985). Also see Jacques et al., Enantiomers, Racemates and Resolutions, Chapter 3 (1981) incorporated herein by reference.

With the exception of the preferential crystallization process when applied to true conglomerates, the prior art processes typically produce a first mixture that is essentially an enantiomerically enriched racemic composition. A number of crystallizations are required to yield the substantially pure enantiomer.

OBJECTS OF THE INVENTION

It is an object of the present invention to provide a process for obtaining a substantially pure enantiomer of an aryl-substituted aliphatic or cycloaliphatic amine.

It is a further object of the present invention to obtain such a substantially pure enantiomer from a composition of enantiomerically enriched aryl-substituted aliphatic or cycloaliphatic amine.

PREFERRED EMBODIMENTS OF THE INVENTION

In the present specification, alkyl means straight or branched chain alkyl having 1 to 20 carbon atoms and includes, for example, methyl, ethyl, propyl, isopropyl, butyl, isobutyl, secondary butyl, tertiary butyl, pentyl, isopentyl, neopentyl, hexyl, heptyl, octyl, 2-ethylhexyl, 1,1,3,3-tetramethylbutyl, nonyl, decyl, dodecyl, tetradecyl, hexadecyl, octadecyl and eicosyl;

cycloalkyl means cyclic alkyl having 3 to 7 carbon atoms and includes cyclopropyl, cyclobutyl, cyclopentyl, cyclohexyl and cycloheptyl;

substituted phenyl or substituted naphthyl means phenyl or naphthyl substituted by at least one substituent selected from the group consisting of halogen (chlorine, bromine, fluorine or iodine), amino, nitro, hydroxy, alkyl, alkoxy which means straight or branched chain alkoxy having 1 to 10 carbon atoms, and includes, for example, methoxy, ethoxy, propoxy, isopropoxy, butoxy, isobutoxy, secondary butoxy, tertiary butoxy, pentyloxy, isopentyloxy, hexyloxy, heptyloxy, octyloxy, nonyloxy and decyloxy, haloalkyl which means straight or alkyl having 1 to 8 carbon atoms which is substituted by at least one halogen, and includes, for example, chloromethyl, bromomethyl, fluoromethyl, iodomethyl, 2-chloroethyl, 2-bromoethyl, 2-fluoroethyl, 3chloropropyl, 3-bromopropyl, 3-fluoropropyl, 4-chlorobutyl, 4-fluorobutyl, dichloromethyl, dibromomethyl, difluoromethyl, diiodomethyl, 2,2-dichloroethyl, 2,2-dibromoethyl, 2,2difluoroethyl, 3,3-dichloropropyl, 3,3-difluropropyl, 4,4dichlorobutyl, 4,4-difluorobutyl, trichloromethyl, trifluoromethyl, 2,2,2-trifluoroethyl, 2,3,3-trifluoropropyl, 1,1,2,2-tetrafluoroethyl and 2,2,3,3-tetrafluoropropyl;

haloalkyl means straight or branched chain alkyl having 1 to 10 carbon atoms which is substituted at least one halogen as mentioned above;

hydroxyalkyl means that the alkyl moiety is straight or branched chain alkyl having 1 to 8 carbon atoms, and includes, for example, hydroxymethyl, 2-hydroxyethyl, 3-hydroxypropyl, 4-hydroxybutyl, 6-hydroxyhexyl, 8-hydroxyoctyl, 1-hydroxyethyl, 1-hydroxy-2-propyl, 2-hydroxypropyl, 2,3-dihydroxypropyl, 1,3-dihydroxy-2-propyl;

alkoxyalkyl means that the alkoxy moiety and the alkyl moiety each are straight or branched chain ones having 1 to 8 carbon atoms, and includes, for example, methoxymethyl, ethoxymethyl, propoxymethyl, isopropoxymethyl, butoxymethyl, isobutoxymethyl, tertiary butoxymethylv pentyloxymethyl, hexyloxymethyl, heptyloxymethyl, octyloxymethyl, 2-methoxyethyl, 2-ethoxyethyl, 2-propoxyethyl, 2-butoxyethyl, 2-hexyloxyethyl, 2octyloxyethyl, 3-methoxypropyl, 3-ethoxypropyl, 3-propoxypropyl, 3-butoxypropyl, 3-hexyloxypropyl, 3-octyloxypropyl, 4-methoxybutyl, 4-ethoxybutyl, 4-propoxybutyl, 4-butoxybutyl, 4-hexyloxybutyl, 4-octyloxybutyl, 5-methoxypentyl, 5-ethoxypentyl, 5-propoxypentyl, 5-butoxypentyl, 5-pentyloxypentyl, 5-hexyloxypntyl, 5-octyloxypentyl, 6-propoxyhexyl, 6-butoxyhexyl, 6-pentyloxyhexyl, 6-hexyloxyhexyl, 6-oxtyloxyhexyl, 8-methoxyoctyl, 8-ethoxyoctyl, 8-butoxyoctyl, 8hexyloxyoctyl and 8-octyloxyoctyl;

acyloxyalkyl means that the acyl moiety is alkanoyl having 2 to 18 carbon atoms, benzoyl, substituted benzoyl, heteroarylcarbonyl or substituted heteroarylcarbonyl and the alkyl moiety is straight or branched chain alkyl having 1 to 8 carbon atoms, and includes, for example, acetoxymethyl, 2-acetoxyethyl, 3-acetoxypropyl, 4-acetoxybutyl, 6-acetoxyhexyl, 8-acetoxyoctyl, propionyloxymethyl, 2-propionyloxyethyl, 3-propionyloxypropyl, 4-propionyloxybutyl, 6-propionyloxyhexyl, 8-propionyloxyoctyl, isobutyryloxymethyl, 2-isobutyryloxyethyl, 4-isobutyryloxybutyl, pivaloytoxymethyl, 2-pivaloyloxyethyl, 4-pivaloyloxybutyl, butyryloxymethyl, 2-butyryloxyethyl, 4-butyryloxybutyl, valeryloxymethyl, 2-valeryloxyethyl, 4-valeryloxybutyl, hexanoyloxymethyl, 2-hexanoyloxyethyl, 4-hexanoyloxybutyl, octanoyloxymethyl, 2-octanoyloxyethyl, 4-octanoyloxybutyl, lauroyloxymethyl, 2-lauroyloxyethyl, 4-lauroyloxybutyl, stearoyloxymethyl, 2-stearoyloxyethyl, 4-stearoyloxybutyl, benzoyloxymethyl, 2-benzoyloxyethyl, 4-benzoyloxybutyl, furoyloxymethyl, 2-furoyloxyethyl, 4-furoyloxybutyl, thenoyloxymethyl, 2-thenoyloxyethyl, 4-thenoyloxybutyl, nicotinoyloxymethyl, 2-nicotinoyloxyethyl and 4-nicotinoyloxybutyl;

carboxyalkyl means that the alkyl moiety is straight or branched chain alkyl having 1 to 8 carbon atoms and includes, for example, carboxymethyl, 2-carboxymethyl, 3-carboxypropyl, 4-carboxybutyl, 6-carboxyhexyl and 8-carboxyoctyl;

alkoxycarbonylalkyl means that the alkoxy moiety and the alkyl moiety each are straight or branched chain ones having 1 to 8 carbon atoms, and includes, for example, methoxycarbonylmethyl, ethoxycarbonylmethyl, propoxycarbonylmethyl, isopropoxycarbonylmethyl, butoxycarbonylmethyl, isobutoxycarbonylmethyl, tertiary butoxycarbonylmethyl, pentlyoxycarbonylmethyl, hexyloxycarbonylmethyl, octyloxycarbonylmethyl, 2-methoxycarbonylethyl, 2-ethoxycarbonylethyl, 2-propoxycarbonylethyl, 2-butoxycarbonylethyl, 3-methoxycarbonylpropyl, 3-ethoxycarbonylpropyl, 3-propoxycarbonylpropyl, 3-butoxycarbonylpropyl, 4-methoxycarbonylbutyl, 4-ethoxycarbonylbutyl, 4-propoxycarbonylbutyl, 4-butoxycarbonylbutyl, 6-methoxycarbonylhexyl, 6-ethoxycarbonylhexyl, 8-methoxycarbonyloctyl and 8-ethoxycarbonyloctyl; and cyanoalkyl means that the alkyl moiety is straight or branched chain alkyl having 1 to 8 carbon atoms and includes, for example, cyanomethyl, 2-cyanoethyl, 3-cyanopropyl, 4-cyanobutyl, 6-cyanohexyl and 8-cyanooctyl.

It should be noted that the above definitions are encompassed within the term "hydrocarbyl" as used herein.

The objective of the present invention is achieved by starting with an enantiomerically enriched mixture of a hydrocarbyl amine in an inert solvent. These materials have the following formula:

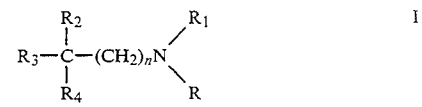

where $R_1$ and $R_2$ are different and are hydrogen, alkyl, cycloalkyl., phenyl, substituted phenyl, naphthyl or substituted naphthyl; $R_2$, $R_3$ and $R_4$ are different and are hydrogen, alkyl, cycloalkyl, phenyl, substituted haloalkyl, hydroxyalkyl, alkoxyalkyl, acyloxyalkyl, carboxyalkyl, alkoxycarbonylalkyl or cyanoalkyl and n is 0 or 1.

Preferred compounds of Formula I are illustrated by phenyl, naphthyl, substituted naphthyl:

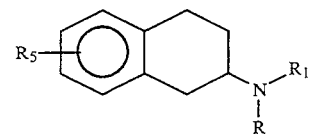

and

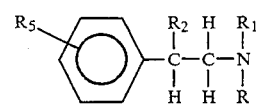

where R, $R_1$ and $R_2$ are as previously defined and $R_5$ is alkyl, alkoxy, acyloxyalkyl, or halo.

Particularly preferred are the following:

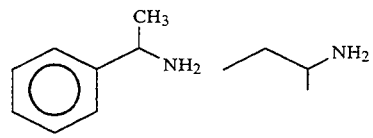

The process of the present invention is particularly applicable to α-methylbenzylamine and especially in obtaining a preponderance of the S isomer.

The invention is carried out by using a mixture of both the (+)and (−) (or dextro and levo rotatory forms) containing a preponderance of one of the enantiomers of the amines of formula I. However, it should be understood that the process itself does not convert one form of the stereoisomers to the other form but only separates such forms. Further in the preferred embodiment of this invention, the separation of enantiomers gives rise to a soluble product largely containing one enantiomer and an insoluble product largely containing the other enantiomer. As such, a high purity product is obtained that requires a minimum number of recrystallizations (usually not more than two) to give a product with exceptionally high optical purity.

The first step in the reaction sequence for the separation of the enriched mixtures used in the present invention is to form a salt of the hydrocarbyl amine of formula I with an optically inactive acid. The acid is preferably an inorganic acid. The inorganic acids are most preferably mineral acids, like HCl, $H_2SO_4$, $H_3PO_4$, HBr, $HClO_4$, etc. Acid can be an organic acid, like acetic, benzoic, etc.

However, it should be noted that the only criteria for such inorganic acid is that it take part in no other reaction with the hydrocarbyl except salt formation and that it be soluble in the solution first used in the process of the present invention. Preferred inorganic acids are hydrobromic acid, sulfuric acid and hydrochloric acid.

The amount of optically inactive acid added to the amine of formula I may be less than, equal to or more than the molar amounts of such amine. However, it is preferred that the acid have a ratio of from about 0.15 to about 0.95 mole per mole of amine of formula I, most preferably from about 0.2 to 0.6 mole per mole of enantiomerically enriched hydrocarbyl amine of formula I.

As a second step in the reaction sequence, an inert solvent is added. The solvent should be inert to the starting materials and the products. Conveniently, with the proper selection of solvents, a solid crystalline material will precipitate from the reaction mixture.

Any solvent that is not reactive with these amines is acceptable. Thus, various aliphatic hydrocarbon solvents, i.e., hexane, heptane, octane, etc., aromatic hydrocarbon solvents, i.e., benzene, toluene, xylene, alcohol solvents, i.e., methanol, ethanol, 1-propyl alcohol, etc., and water are preferred for such solvent. Particularly preferred are the aliphatic hydrocarbon solvents, especially hexane. It should be understood that mixtures of such solvents are also encompassed within the meaning of "inert solvent".

At this point in the reaction sequence (after the admixture of the solvent with the acid and the enriched hydrocarbyl amine, the salt and solvent may be heated, e.g. to a temperature of about 25° C. to about 125° C., preferably about 75° C. to 120° C. or the heating can occur before the salt solution is formed. Heating is typically carried out from about 1 to about 16 hours, preferably from about 2 to about 8 hours.

It is preferred that the solvent, acid, hydrocarbyl amine to acid stoichiometry and temperature are selected so that the number of moles of salt precipitating is less than the number of moles of enriched amine initially charged.

Each of the salts formed 1 from the reaction of optically inactive inorganic acid with aliphatic hydrocarbyl amines of formula I exhibits a unique solubility phase diagram, i.e. a plot of the solubility versus enantiomeric composition.

The eutectic point in such phase diagrams represents the most soluble composition of the mixture of enantiomers. If a solid enriched mixture of enantiomers is admixed with a solvent, either all or part of the mixture will dissolve. If a sufficient amount of solvent is added so that the entire mixture becomes a solution, then cooling the solution (or evaporating some of the solvent or adding a nonsolvent, or any other conventional method used to precipitate solutes from solutions) will precipitate a portion of the salt. Depending on where the eutectic point lies, the precipitated salt may be more highly enriched in one of the enantiomers or it may approach the composition of the racemic mixture. If the latter case occurs, obviously, the mother liquor will be more highly enriched than the initial hydrocarbyl amine enriched with one of the enantiomers.

Thus, the substantially pure salt formed from the enriched mixtures of compounds of formula I must have the following properties:

i ) at least one eutectic point;

ii) a composition that is not at the eutectic point; and iii) a eutectic composition that is closer to the racemic composition than it is to the eutectic composition of the the compounds represented by formula I, or be a solid where compound I is a liquid.

In the phase diagram then, if the eutectic point is at the racemic composition, an enantiomeric mixture of 70% S(+) [and 30% R(−)] upon cooling preferentially forms the most soluble fraction of 50% S(+) and 50% R(−) [the racemic composition]. The precipitated product will then have a higher concentration of S(+) than the starting composition.

Conversely, where the starting enantiomeric enriched mixture is 30% S(+) [and 70% R(−)], the precipitated product will have a higher concentration of the R(−) enantiomer. It is less soluble than the racemic mixture which preferentially forms.

While the term "precipitated product" (or salt) is used in various places throughout this specification, it should be noted that a similar purification can occur by adding smaller amounts of solvent than would be required to completely dissolve the enriched salt. This preferential leaching or extraction process produces identical results as precipitation from solutions.

The crystalline residue separated in the above step is substantially pure enantiomeric material. However, it should be understood that the actual purity of such "substantially pure enantiomer" is dependent on the composition of the starting enantiomerically enriched amine. Thus, by carrying out the process of this invention using an amine of formula I having an optical purity of 70% ee (% ee equals the weight percent of major enantiomer minus the weight percent of minor enantiomer), the process of this invention yields the substantially pure enantiomeric salt, i.e., an 89% ee S pure product. Compositions of greater enrichment in, for example, the S isomer yield final product of even higher purity, i.e., an 80% ee S composition produces the substantially pure enantiomer as 93% ee S pure product. Of course, compositions having smaller amounts of enrichment than the above noted 70% ee S produce final product of less than 89% ee S. The relationship between composition of the starting amine and composition of the final amine is surprisingly linear. The process of this invention provides, in one step, a product that is obtained by the prior art processes mentioned earlier in numerous steps. As such, the process provides a more simplified method of obtaining highly pure enantiomeric salts of the amines of formula I than previously available.

The purified salt obtained from the process of the present invention may be further treated to produce the free amine by using any conventional means. For example, hydrolysis of the salt with a dilute inorganic base and extraction with a suitable organic solvent produces the purified hydrocarbyl amine. Further extraction and recrystallization with a suitable solvent can increase the purity to even a greater extent.

The following examples are for illustration only and is not intended as limiting the invention in any way.

EXAMPLES

Example 1

Optical Purification of HPAT.HBr

To a solution of 326 g (1.14 mole) of 5-hydroxy-2propylaminotetralin hydrobromide (HPAT.HBr) with a specific rotation of −39°(c=1,CH$_3$OH) in 2000 mL of methanol at about 50° C., was slowly added 1500 mL of 2-propanol and the mixture was concentrated to ~2000 mL. It was allowed to cool to room temperature by stirring overnight. The precipitated salt was filtered, washed with 2-propanol (100 mL) and dried to obtain 278 g of the hydrobromide with a specific rotation of −54°.

The salt was recrystallized again by dissolving in 1.0 L of hot methanol, adding 1.5 L of 2-propanol, concentrating the mixture to 2 L and then cooling to room temperature. Yield of the salt =203 g and the specific rotation of the salt = −62°.

Thus, optical purity of HPAT.HBr increased from 63% ee to 100%ee by direct crystallization.

Example 2

Optical Purification of α-Methylbenzylamine (MBA) via the Sulfate Salt - Purification in the precipitated Salt The enantiomeric compositions of MBA samples were determined by gas chromatography on a chiral column.

To a solution of 5.0 g (41 mmol) of α-methylbenzylamine (MBA) containing 70% S-isomer and 30% R-isomer in 25 mL of hexane was slowly added 1.0 g (9.9 mmol) of 97% sulfuric acid. The resulting mixture was stirred at ambient temperature for 8 h and the white solid was removed by filtration. Drying in vacuo afforded 3.5 g (100% yield) of 2MBA.H$_2$SO$_4$. A portion of this was partitioned between 1N HCl and hexane and chiral GC analysis of the liberated MBA in the hexane layer showed it to be 89% S-isomer and 11% R-isomer.

Example 3

Optical Purification of α-Methylbenzylamine (MBA) via the Chloride Salt - purification in the Mother Liquor To a solution of 5.0 g (41 mmol) of α-methylbenzylamine (MBA) containing 80% S-isomer and 20% R-isomer in 25 mL of diethyl ether was slowly added 20 mL of 1M HCl (20 mmol) in diethyl ether. The resulting mixture was stirred at ambient temperature for 2 h and the white solid was removed by filtration. Drying in vacuo afforded 3.2 g (100% yield) of MBA.HCl. A portion of this was partitioned between 1N HCl and hexane and chiral GC analysis of the liberated MBA in the hexane layer showed it to be 70% S-isomer and 30% R-isomer. Chiral GC analysis of the filtrate showed the free MBA contained therein to be 93% S-isomer and 7% R-isomer.

Example 4

Optical Purification of β-Methylphenethylamine (MPA) via the Chloride Salt

To a solution of 2.7 g (20 mmol) of β-Methylphenethylamine (MPA), with an optical purity of 80%ee, in 40 mL of diethyl ether was slowly added 10 mL of 1M HCl (10 mmol) in diethyl ether. A thick white percipitate was formed. The mixture was stirred at room temperature for 2 hours and the precipitated solid was isolated by filtration. Drying in vacuo afforded 1.6 g (94% yield) of MPA.HCl. Optical purity of this salt was found to be 92%ee by chiral GC analysis. 1.4 g of the free amine was recovered from the filtrate and its purity was 66%ee.

We claim:

1. A process for producing a substantially pure enantiomeric salt of a hydrocarbyl amine having the formula:

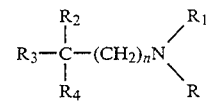

where R$_1$ and R$_2$ are different and are hydrogen, alkyl, cycloalkyl, phenyl, substituted phenyl, naphthyl, substituted naphthyl; R$_3$, R$_4$ and R$_5$ are different and are hydrogen, alkyl, cycloalkyl, phenyl, naphthyl, substituted phenyl, substituted naphthyl, haloalkyl, hydroxyalkyl, alkoxyalkyl, acyloxyalkyl, carboxyalkyl, alkoxycarbonylalkyl or cyanoalkyl; and n is 0 or 1; which comprises:

i) reacting said hydrocarbyl amine enriched with one of its enantiomers with an optically inactive acid thereby forming a salt of said hydrocarbyl amine enriched with said enantiomer, said salt having: a) at least one eutectic point; b) a composition that is not at the eutectic point; and c) a eutectic composition that is closer to the racemic composition than is the eutectic composition of said hydrocarbyl amine, or be a solid where compound I is a liquid;

ii) treating said salt with an inert solvent;

iii) separating a salt of the substantially pure enantiomer of the hydrocarbyl amine.

2. The process according to claim 1 wherein said inorganic acid is a mineral acid.

3. The process according to claim 2 wherein said mineral acid is an aqueous solution of an oxide or halide of a Group VB or VIB element of the Periodic Table of Elements.

4. The process according to claim 3 wherein said inorganic acid is selected from the group hydrochloric acid, hydrobromic acid and sulfuric acid.

5. The process of claim 1 wherein the solvent for said of step ii) is a inert organic solvent.

6. The process according to claim 1 wherein the ratio of said acid is from about 0.2 to about 0.95 mole per mole of enantiomerically enriched hydrocarbyl amine.

7. The process according to claim 6 wherein the ratio is from about 0.4 to about 0.6 made per mole of enantiomerically enriched hydrocarbyl amine.

8. The process of claim 1 wherein said hydrocarbyl amine enriched with one of its enantiomers is treated with said base at a temperature of from about 25° C. to about 125° C.

9. The process according to claim 1 wherein $R_2$ is hydrogen, $R_3$ is methyl and $R_4$ is phenyl.

10. The process of claim 9 wherein the enantiomerically enriched hydrocarbyl amine is obtained from a diastereomeric crystallization process.

11. The process of claim 9 wherein the enantiomerically enriched hydrocarbyl amine is obtained from a catalyzed kinetic resolution process.

12. The process according to claim 11 wherein said catalyzed kinetic resolution process is carried out with a chemical catalyst.

13. The process according to claim 11 wherein said catalyzed kinetic resolution process is carried out with a biological catalyst.

14. The process according to claim 1 wherein said enantiomerically enriched hydrocarbyl amine is obtained from a catalyzed asymmetric synthesis.

15. The process according to claim 14 wherein the catalyst is a chemical catalyst.

16. The process according to claim 14 wherein the catalyst is a biological catalyst.

* * * * *